United States Patent
Ta et al.

(10) Patent No.: US 11,304,833 B2
(45) Date of Patent: Apr. 19, 2022

(54) INTRAVASCULAR STENT HAVING HIGH FATIGUE PERFORMANCE

(71) Applicant: Abbott Cardiovascular Systems Inc., Santa Clara, CA (US)

(72) Inventors: Diem Uyen Ta, San Jose, CA (US); Senthil Kumar Eswaran, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 2 days.

(21) Appl. No.: 16/802,495

(22) Filed: Feb. 26, 2020

(65) Prior Publication Data
US 2020/0188146 A1    Jun. 18, 2020

Related U.S. Application Data

(62) Division of application No. 15/950,486, filed on Apr. 11, 2018, now Pat. No. 10,575,973.

(51) Int. Cl.
*A61F 2/89* (2013.01)
*A61F 2/958* (2013.01)

(52) U.S. Cl.
CPC .............. *A61F 2/89* (2013.01); *A61F 2/958* (2013.01); *A61F 2210/0004* (2013.01); *A61F 2230/006* (2013.01); *A61F 2230/0013* (2013.01); *A61F 2230/0056* (2013.01); *A61F 2230/0069* (2013.01)

(58) Field of Classification Search
CPC ................ A61F 2/90; A61F 2002/9155; A61F 2002/061; A61F 2/89; A61F 2230/006; A61F 2230/0013; A61F 2230/0056; A61F 2002/828; A61F 2002/91575; A61F 2/915; A61F 2/958; A61F 2210/0004; A61F 2230/0069
See application file for complete search history.

(56) References Cited

U.S. PATENT DOCUMENTS

| | | | | |
|---|---|---|---|---|
| 2015/0374521 A1* | 12/2015 | Zheng | ...................... | A61F 2/844 623/1.2 |
| 2018/0010230 A1* | 1/2018 | Boyle | ...................... | A61F 2/915 |
| 2018/0360630 A1* | 12/2018 | Kim | ........................ | A61F 2/915 |

* cited by examiner

*Primary Examiner* — Brian A Dukert
*Assistant Examiner* — Rebecca Lynee Zimmerman
(74) *Attorney, Agent, or Firm* — Fulwider Patton LLP

(57) ABSTRACT

The invention is directed to an expandable stent for implantation in a body lumen, such as an artery, and a method for making it from a single length of tubing. The stent consists of a plurality of radially expandable cylindrical elements generally aligned on a common axis and interconnected by one or more links. A Y-shaped member comprised of a link and a U-shaped member has relief dimples formed in the curved portion of a valley to reduce localized stress and thereby reduce fatigue failure that can lead to link structure failure.

6 Claims, 5 Drawing Sheets

INTRAVASCULAR STENT HAVING HIGH FATIGUE PERFORMANCE

The present application is a division of U.S. application Ser. No. 15/950,486, filed Apr. 11, 2018, which is hereby incorporated by reference.

BACKGROUND

This invention relates to expandable endoprosthesis devices, generally called stents, which are adapted to be implanted into a patient's body lumen, such as blood vessel, to maintain the patency thereof. These devices are very useful in the treatment of atherosclerotic stenosis in blood vessels.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

The stent must be able to satisfy a number of mechanical requirements. First, the stent must be capable of withstanding the structural loads, namely radial compressive forces, imposed on the stent as it supports the wall of a vessel. Therefore, a stent must possess adequate radial strength. Radial strength, which is the ability of a stent to resist radial compressive forces, is due to strength and rigidity around the circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Along with crimping and expansion forces, implanting a stent in the dynamic environment in a curved artery section causes stresses in the stent structure that can result in fatigue failure. This fatigue failure is particularly acute in stents formed from a polymer material.

What has been needed and heretofore unavailable is a stent formed from a polymer material and modified in critical structural areas where cyclical loads are concentrated, and fatigue stresses are constant in order to improve the fatigue performance of the stent.

SUMMARY OF THE INVENTION

The present invention is directed to an expandable stent which is relatively flexible along its longitudinal axis to facilitate delivery through tortuous body lumens, but which has structural features to improve fatigue performance of the stent.

The stent of the invention generally includes a plurality of radially expandable cylindrical elements or rings which are relatively independent in their ability to expand and to flex relative to one another. Interconnecting elements or links extending between adjacent cylindrical rings provide increased stability and prevent warping of the stent upon the expansion thereof. The resulting stent structure is a series of radially expandable cylindrical rings which are spaced longitudinally close enough so that small dissections in the wall of a body lumen may be pressed back into position against the lumenal wall, but not so close as to compromise the longitudinal flexibility of the stent.

Each of the cylindrical rings making up the stent has a proximal end and a distal end and a cylindrical plane defined by a cylindrical outer wall surface that extends circumferentially between the proximal end and the distal end of the cylindrical ring. Generally the cylindrical rings have a serpentine or undulating shape which includes at least one U-shaped element, and typically each ring has more than one U-shaped element. The cylindrical rings are interconnected by at least one link which attaches one cylindrical ring to an adjacent cylindrical ring. The combination of the rings and links allows the stent to be highly flexible along its longitudinal axis.

Not only do the links that interconnect the cylindrical rings provide flexibility to the stent, but the positioning of the links also enhances the flexibility by allowing uniform flexibility when the stent is bent in any direction along its longitudinal axis. Uniform flexibility along the stent derives in part from the links of one ring being circumferentially offset from the links in an adjacent ring. Further, the cylindrical rings are configured to provide flexibility to the stent in that portions of the rings can flex or bend as the stent is delivered through a tortuous vessel.

The cylindrical rings typically are formed of a plurality of peaks and valleys, where the valleys of one cylindrical ring are in phase with the valleys of an adjacent cylindrical ring. In this configuration, at least one link attaches each cylindrical ring to an adjacent cylindrical ring so that at least a portion of the link is positioned within one of the valleys and it attaches the valley to an adjacent peak.

While the cylindrical rings and links generally are not separate structures, they have been conveniently referred to as rings and links for ease of identification. Further, the cylindrical rings can be thought of as comprising a series of U's, W's and Y-shaped structures in a repeating pattern. Again, while the cylindrical rings are not divided up or segmented into U's, W's and Y's, the pattern of the cylindrical rings resemble such configurations. The U's, W's and Y's promote flexibility in the stent primarily by flexing as the stent is delivered through a tortuous vessel.

The radial expansion of the expandable ring deforms the undulating pattern thereof similar to changes in a waveform which result in decreasing the waveform's amplitude. Preferably, the undulating patterns of the individual cylindrical structures are in phase with each other in order to prevent the contraction of the stent along its length when it is expanded. The cylindrical structures of the stent are plastically deformed when expanded (except with NiTi alloys) so that the stent will remain in the expanded condition, therefore they must be sufficiently rigid when expanded to prevent the collapse thereof in use.

The links which interconnect adjacent cylindrical rings should have a transverse cross-section similar to the transverse dimensions of the undulating components of the expandable cylindrical rings. The links may be formed in a unitary structure with the expandable cylindrical rings from the same intermediate product, such as a tubular element. Preferably, all of the links of a stent are joined at either the peaks or the valleys of the undulating structure of the cylindrical rings which form the stent. In this manner, there is no shortening of the stent upon expansion.

The number and location of the links interconnecting adjacent cylindrical rings can be varied in order to develop the desired longitudinal flexibility in the stent structure both in the unexpanded as well as the expanded condition. These properties are important to minimize alteration of the natural physiology of the body lumen into which the stent is implanted and to maintain the compliance of the body lumen which is internally supported by the stent. Generally, the greater the longitudinal flexibility of the stent, the easier and the more safely it can be delivered to the implantation site.

In one embodiment, the Y-shaped members are formed by the link attaching to a curved portion of a valley, which then resembles the Y-shaped member. In this embodiment, there is a gradual radius on each side of the link where it connects to the curved portion of the Y-shaped member. More specifically, a smooth and gradual transition radius extends from each side of the link to the curved portion of the Y-shaped member, the radius being in the range from 0.017 to 0.022 inch (0.44 to 0.55 mm). One preferred radius is 0.019 inch (0.50 mm). These gradual and smooth transition radii provide a more ridged and stiffer scaffold area resulting in improved link structural fatigue performance.

In another embodiment, the Y-shaped members are formed by the links attaching to a curved portion of a valley, which then resembles the Y-shaped member. In this embodiment, the curved portion of the valley has a width that is less than the width of the curved portion of the peaks forming the U-shaped members. In one embodiment, the width of the curved portion of the valley of the Y-shaped member is in the range from 0.0073 to 0.0066 inch (0.185 to 0.168 mm). In one preferred embodiment, the width of the curved portion of the valley of the Y-shaped member is 0.0068 inch (0.173 mm). This Y-shaped member provides a reduced width which will experience less stress during fatigue loading, and hence result in improved Y-shaped member structural fatigue performance.

In another embodiment, the Y-shaped members are formed by the links attaching to a curved portion of a valley, which then resembles the Y-shaped member. In this embodiment, relief dimples are formed in the curved portion of the valley where the link attaches to the curved portion. Link fatigue factures can occur at the end of a straight strut segment near the link and valley junction where the material is highly stressed during fatigue loading and fatigue strength is lower due to the axially oriented material being weaker. The purpose of introducing relief dimples on the curved portion of the valley is to shift the location of this highly stressed area more into the curved portion of the valley where the circumferentially oriented material is stronger and can withstand more stress, thereby improving structural fatigue performance.

Other features and advantages of the present invention will become more apparent from the following detailed description of the invention, when taken in conjunction with the accompanying exemplary drawings.

DETAILED DESCRIPTION OF THE PREFERRED EMBODIMENTS

Figure 1:
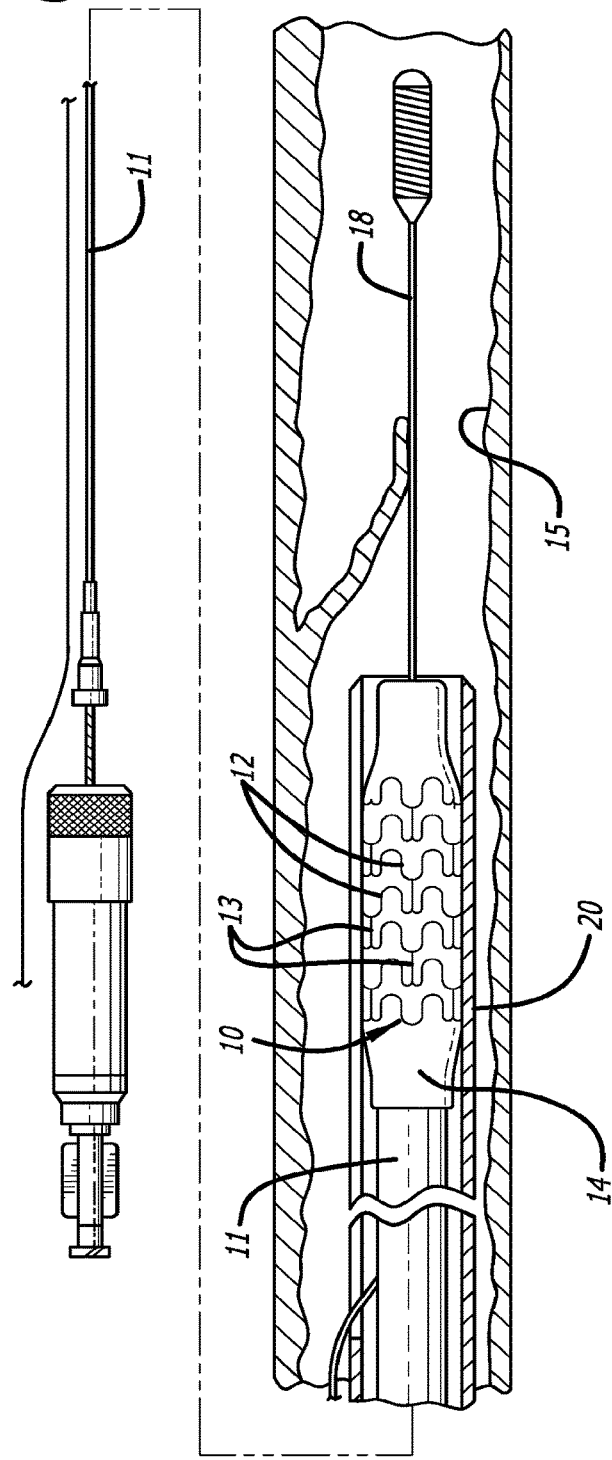
FIG. 1 is an elevational view, partially in section, of a stent embodying features of the invention which is mounted on a delivery catheter and disposed within a damaged artery.

FIG. 1 illustrates a prior art stent 10 which is mounted onto a delivery catheter 11. The stent generally comprises a plurality of radially expandable cylindrical rings 12 disposed generally coaxially and interconnected by links 13 disposed between adjacent cylindrical rings. The delivery catheter 11 has an expandable portion or balloon 14 for expanding of the stent 10 within an artery 15.

The delivery catheter 11, onto which the stent 10 is mounted, is similar to a conventional balloon dilatation catheter used for angioplasty procedures.

Each radially expandable cylindrical ring 12 of the stent 10 may be independently expanded. Therefore, the balloon 14 may be provided with an inflated shape other than cylindrical, e.g. tapered, to facilitate implantation of the stent 10 in a variety of body lumen shapes.

Figure 2:
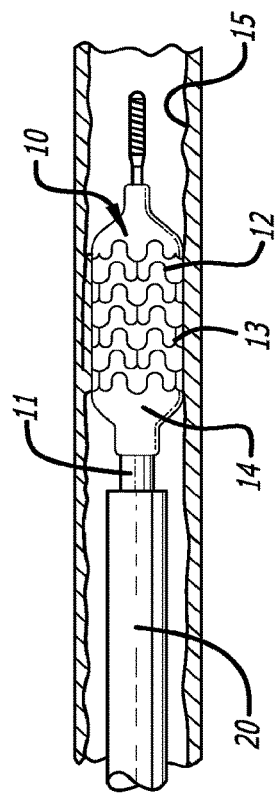
FIG. 2 is an elevational view, partially in section, similar to that shown in FIG. 1 wherein the stent is expanded within a damaged artery, pressing the damaged lining against the arterial wall.

The delivery of the stent 10 is accomplished in the following manner. The stent 10 is first mounted onto the inflatable balloon 14 on the distal extremity of the delivery catheter 11. The balloon 14 is slightly inflated to secure the stent 10 onto the exterior of the balloon. The catheter-stent assembly is introduced within the patient's vasculature in a conventional Seldinger technique through a guiding catheter (not shown). A guidewire 18 is disposed across an arterial section and then the catheter-stent assembly is advanced over a guidewire 18 within the artery 15 until the stent 10 is positioned in the area to be repaired. The balloon 14 of the catheter 11 is expanding the stent 10 against the artery 15, which is illustrated in FIG. 2. While not shown in the drawing, the artery 15 is preferably expanded slightly by the expansion of the stent 10 to seat or otherwise fix the stent 10 to prevent movement. In some circumstances, during the treatment of stenotic portions of an artery, the artery may have to be expanded considerably in order to facilitate passage of blood or other fluid there through.

Figure 3:
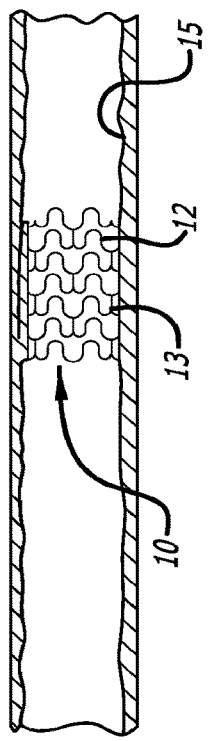
FIG. 3 is an elevational view, partially in section showing the expanded stent within the artery after withdrawal of the delivery catheter.

The stent 10 serves to hold open the artery 15 after the catheter 11 is withdrawn, as illustrated by FIG. 3. Due to the formation of the stent 10 from an elongated tubular member, the undulating component of the cylindrical rings of the stent 10 is relatively flat in transverse cross-section, so that when the stent is expanded, the cylindrical rings are pressed slightly into the wall of the artery 15, and as a result, do not interfere with the blood flow through the artery 15. The cylindrical rings 12 of stent 10 which are pressed into the wall of the artery 15 will eventually be covered with endothelial cell growth which further minimizes blood flow interference. The undulating portion of the cylindrical rings 12 provide good tacking characteristics to prevent stent movement within the artery. Furthermore, the closely spaced cylindrical rings 12 at regular intervals provide uniform support for the wall of the artery 15.

Figure 4:
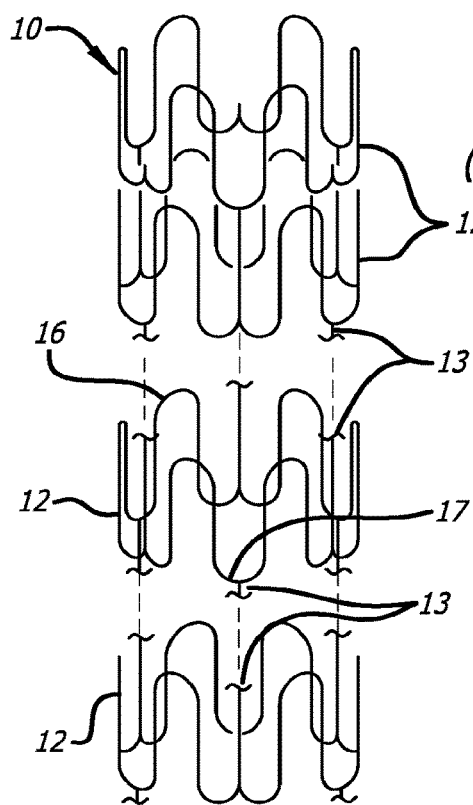
FIG. 4 is a perspective view of a stent embodying features of the invention in an unexpanded state, with one end of the stent being shown in an exploded view illustrate the details thereof.
Figure 5:
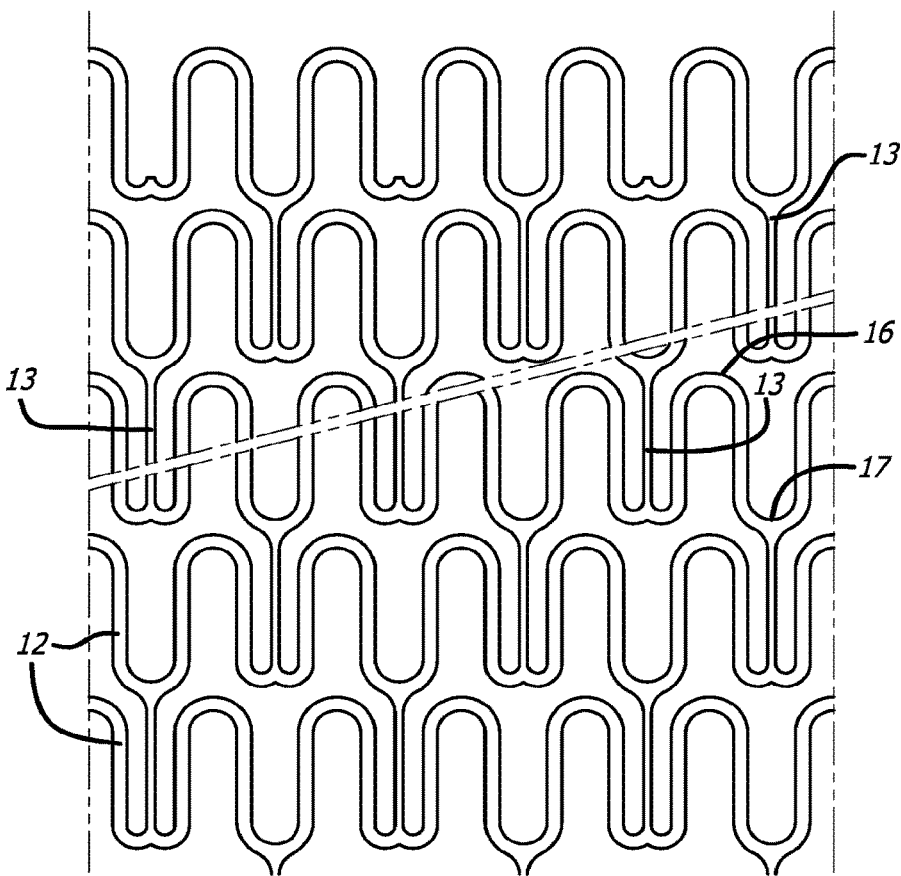
FIG. 5 is a plan view of a flattened section of a stent of the invention which illustrates the undulating pattern of the stent shown in FIG. 4.

FIG. 4 is an enlarged perspective view of the prior art stent 10 shown in FIG. 1 with one end of the stent shown in an exploded view to illustrate in greater detail the placement of links 13 between adjacent radially expandable cylindrical rings. Each pair of the links 13 on one side of a cylindrical ring 12 are preferably placed to achieve maximum flexibility for a stent. As shown in FIGS. 4 and 5, the stent 10 has three links 13 between adjacent radially expandable cylindrical rings 12 which are 120 degrees apart. Each pair of links 13 on one side of a cylindrical element 12 are offset radially 60 degrees from the pair on the other side of the cylindrical ring. The alternation of the links results in a stent which is longitudinally flexible in essentially all directions. Various configurations for the placement of links are possible. All of the links of an individual stent should be secured to either peaks 16 or valleys 17 of the undulating structural rings in order to prevent shortening of the stent during expansion thereof.

Figure 6:
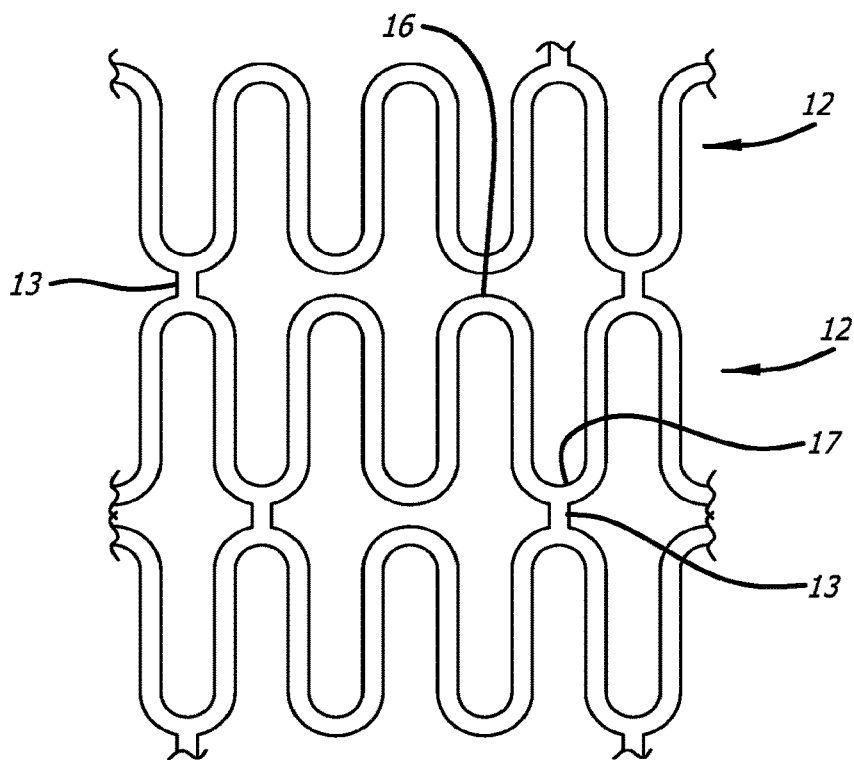
FIG. 6 is a plan view of a flattened section of a stent illustrating an alternate undulating pattern in which the expandable cylindrical elements of the stent which are out of phase.

The properties of the stent 10 may also be varied by alteration of the undulating pattern of the cylindrical rings 12. FIG. 6 illustrates an alternative prior art stent structure in which the cylindrical rings are in serpentine patterns but out of phase with adjacent cylindrical rings. The particular pattern and how many undulations per unit of length around the circumference of the cylindrical rings 12, or the amplitude of the undulations, are chosen to fill particular mechanical requirements for the stent such as radial stiffness.

The number of undulations may also be varied to accommodate placement of links 13, e.g., at the peaks of the undulations as shown in FIGS. 5 and 6.

Figure 7:
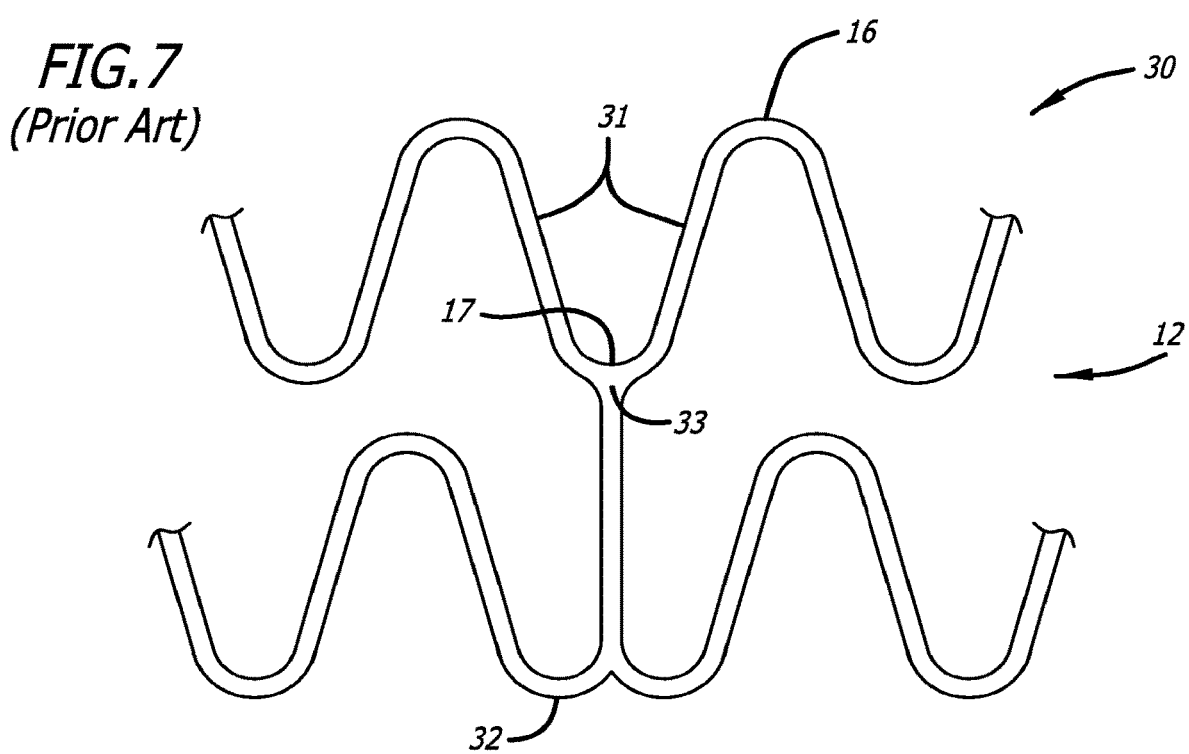
FIG. 7 is an enlarged partial view of the stent of FIG. 5 with the various members slightly expanded.

As shown in FIG. 7, a portion of the prior art stent 10 is slightly expanded to illustrate the expansion of the cylindrical rings 12, which are in the form of a serpentine pattern 30. As previously mentioned, each cylindrical ring 12 is connected by links 13. Serpentine pattern 30 is made up of a plurality of U-shaped members 31, W-shaped members 32, and Y-shaped members 33, each having a different radius so that expansion forces are more evenly distributed over the various members.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

A stent may be fabricated from a polymeric tube or a sheet by rolling and bonding the edges to form a tube. A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

The pattern of a stent can vary throughout its structure to allow radial expansion and compression and longitudinal flexure. A pattern may include portions of struts that are straight or relatively straight, or some patterns may include bending elements. The bending elements can comprise free bending elements, W-shaped bending elements, and Y-shaped bending elements. Bending elements that have a U-shape are free bending elements. The free bending elements are not directly connected to any adjacent ring, whereas each W-shaped bending element is directly connected by one of the links at a concave portion of the apex of the W-shaped bending element to a convex portion of an apex on an adjacent ring located in a direction of a first end of a scaffold, and each Y-shaped bending element is directly connected by one of the links at a convex portion of the apex of the Y-shaped bending element to a concave portion of an apex on an adjacent ring located in a direction of a second end of the scaffold.

Bending elements bend inward when a stent is crimped to allow radial compression. Bending elements also bend outward when a stent is expanded to allow for radial expansion. After deployment, a stent is under static and cyclic compressive loads from the vessel walls. Thus, bending elements are subjected to deformation during use. "Use" includes, but is not limited to, manufacturing, assembling (e.g., crimping stent on a catheter), delivery of stent into and through a bodily lumen to a treatment site, and deployment of stent at a treatment site, and treatment after deployment.

As indicated above, a stent has certain mechanical requirements. A stent must have sufficient radial strength to withstand structural loads, namely radial compressive forces, imposed on the stent as it supports the walls of a vessel. In addition, the stent must possess sufficient flexibility to allow for crimping, expansion, and cyclic loading. Also, a sufficiently low profile is important to deliver the stent to the treatment site.

Polymers tend to have a number of shortcomings for use as materials for stents. One such shortcoming is that many biodegradable polymers have a relatively low modulus, and thus relatively low radial strength. Compared to metals, the strength to weight ratio of polymers is smaller than that of metals. A polymeric stent with inadequate radial strength can result in mechanical failure or recoil inward after implantation into a vessel. To compensate for the relatively low modulus, a polymeric stent requires significantly thicker struts than a metallic stent, which results in an undesirably large profile.

Another shortcoming of polymers is that many polymers, such as biodegradable polymers, tend to be brittle under physiological conditions or conditions within a human body. Specifically, such polymers can have a Tg, which is defined below, above human body temperature which is approximately 37° C. These polymer systems exhibit a brittle fracture mechanism in which there is little or no plastic deformation prior to failure. As a result, a stent fabricated from such polymers can have insufficient toughness for the range of use of a stent. In particular, it is important for a stent to be resistant to fracture throughout the range of use of a stent, i.e., crimping, delivery, deployment, and during a desired treatment period.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised, the actual molecular volume in the sample remains constant, and so a higher coefficient of expansion points to an increase in free volume associated with the system and therefore increases freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

Other potential problems with polymeric stents include creep, stress relaxation, and physical aging. Creep refers to the gradual deformation that occurs in a polymeric construct subjected to an applied load. It is believed that the delayed response of polymer chains to stress during deformation causes creep behavior. Creep occurs even when the applied load is constant. Creep can cause an expanded stent to retract radially inward, reducing the effectiveness of a stent in maintaining desired vascular patency. The rate at which polymers creep depends not only on the load, but also on temperature. In general, a loaded construct creeps faster at higher temperatures.

Stress relaxation is also a consequence of delayed molecular motions as in creep. Contrary to creep, however, which is experienced when the load is constant, stress relaxation occurs when deformation (or strain) is constant and is manifested by a reduction in the force (stress) required to maintain a constant deformation Physical aging, as used herein, refers to densification in the amorphous regions of a semi-crystalline polymer. Physical aging of semi-crystalline polymers that have glass transition temperatures (Tg) above their normal storage temperature, which, for the purposes of this invention is room temperature, i.e., from about 15° C. to about 35° C., occurs primarily through the phenomenon known as densification. Densification occurs when polymer chains rearrange in order to move from a non-equilibrium state to an equilibrium state. The reordering of polymer chains tends to increase the modulus of the polymer resulting in a brittle or more brittle polymer.

Thus, physical aging results in an increase in brittleness of a polymer which can result in cracking of struts upon crimping and deployment. Since physical aging results from densification of amorphous regions of a polymer, an increase in crystallinity can reduce or inhibit physical aging.

However, it is well known by those skilled in the art that the mechanical properties of a polymer can be modified through various processing techniques, such as by applying stress to a polymer. James L. White and Joseph E. Spruiell, Polymer and Engineering Science, 1981, Vol. 21, No. 13. The application of stress can induce molecular orientation along the direction of stress which can modify mechanical properties along the direction of applied stress. For example, strength and modulus are some of the important properties that depend upon orientation of polymer chains in a polymer. Molecular orientation refers to the relative orientation of polymer chains along a longitudinal or covalent axis of the polymer chains.

A polymer may be completely amorphous, partially crystalline, or almost completely crystalline. A partially crystalline polymer includes crystalline regions separated by amorphous regions. The crystalline regions do not necessarily have the same or similar orientation of polymer chains. However, a high degree of orientation of crystallites may be induced by applying stress to a semi-crystalline polymer. The stress may also induce orientation in the amorphous regions. An oriented amorphous region also tends to have high strength and high modulus along an axis of alignment of polymer chains. Additionally, for some polymers under some conditions, induced alignment in an amorphous polymer may be accompanied by crystallization of the amorphous polymer into an ordered structure. This is known as stress induced crystallization.

As indicated above, due to the magnitude and directions of stresses imposed on a stent during use, it is important for the mechanical stability of the stent to have suitable mechanical properties, such as strength and modulus in both the axial and circumferential directions. Therefore, it can be advantageous to modify the mechanical properties of a tube, to be used in the fabrication of a stent, by induced orientation from applied stress in the axial direction, circumferential direction, or both. Since highly oriented regions in polymers tend to be associated with higher strength and modulus, it may be desirable to incorporate processes that induce alignment of polymer chains along one or more preferred axes or directions into fabrication of stents.

Figure 8:
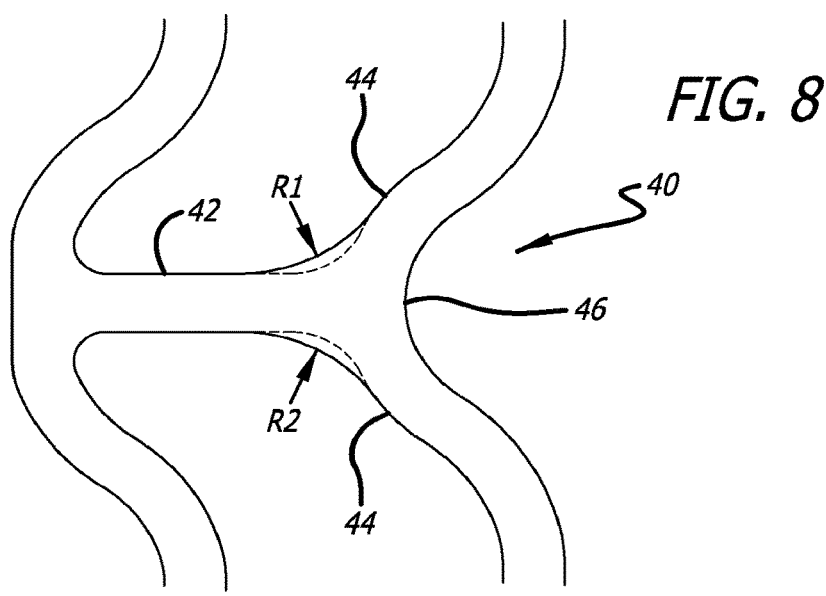
FIG. 8 is an enlarged partial view of a Y-shaped member depicting a smooth and gradual transition radius from the link to the curved portion of the Y-shaped member.

In keeping with the invention shown in FIG. 8, the Y-shaped members 40 are formed by the links 42 attaching to a curved portion 44 of a valley 46, which then resembles the Y-shaped member 40. In this embodiment, there is a gradual radius R1 and R2 on each side of the link where it connects to the curved portion of the Y-shaped member. More specifically, a smooth and gradual transition radius R1 and R2 extends from each side of the link to the curved portion of the Y-shaped member, the radius R1 or R2 being in the range from 0.017 to 0.022 inch (0.44 to 0.55 mm). One preferred radius is 0.019 inch (0.50 mm). This gradual and smooth transition radius provides a more rigid and stiffer scaffold area which will undergo less displacement during fatigue loading resulting in improved link structural fatigue performance. Further, the stiffer Y-transition could develop additional material orientation through crimping resulting in higher material strength in the region.

Figure 9A:
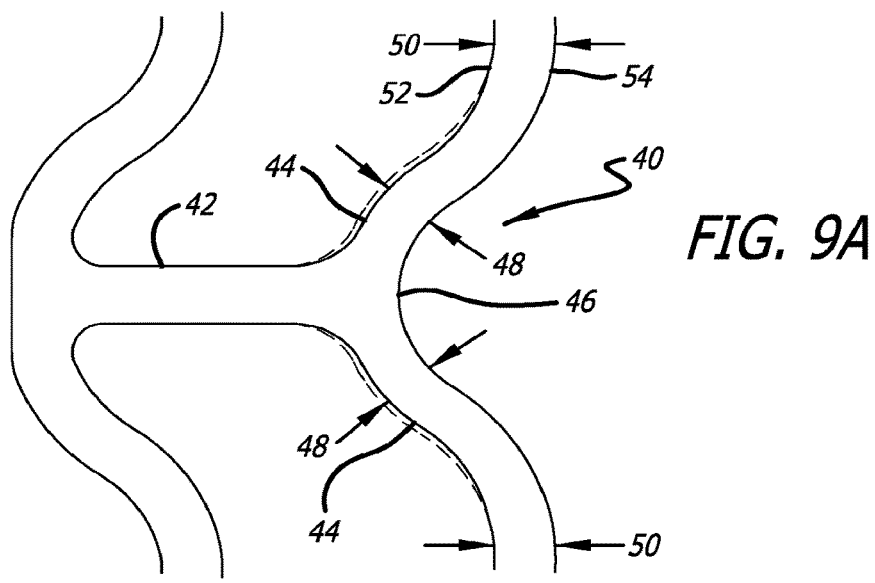
FIGS. 9A-9C are enlarged partial views depicting a Y-shaped member having a narrow width through the curved portion of the Y-shaped member.

In another embodiment as shown in FIG. 9A, the Y-shaped members 40 are formed by the link 42 attaching to a curved portion 44 of a valley 46, which then resembles the Y-shaped member 40. In this embodiment, the curved portion 44 of the valley 46 has a width 48 that is less than a width 50 of the curved portion 52 of the peaks 54 forming the U-shaped members (not shown). In one embodiment, the width 48 of the curved portion of the valley of the Y-shaped member is in the range from 0.0073 to 0.0066 inch (0.185 to 0.168 mm). In one preferred embodiment, the width of the curved portion of the valley of the Y-shaped member is 0.0068 inch (0.173 mm). The width 50 of the curved portion 52 is 0.0075 inch (0.1905 mm). This Y-shaped member is highly flexible and will experience less stress during fatigue loading, and hence result in improved Y-shaped member structural fatigue performance.

Figure 9B:
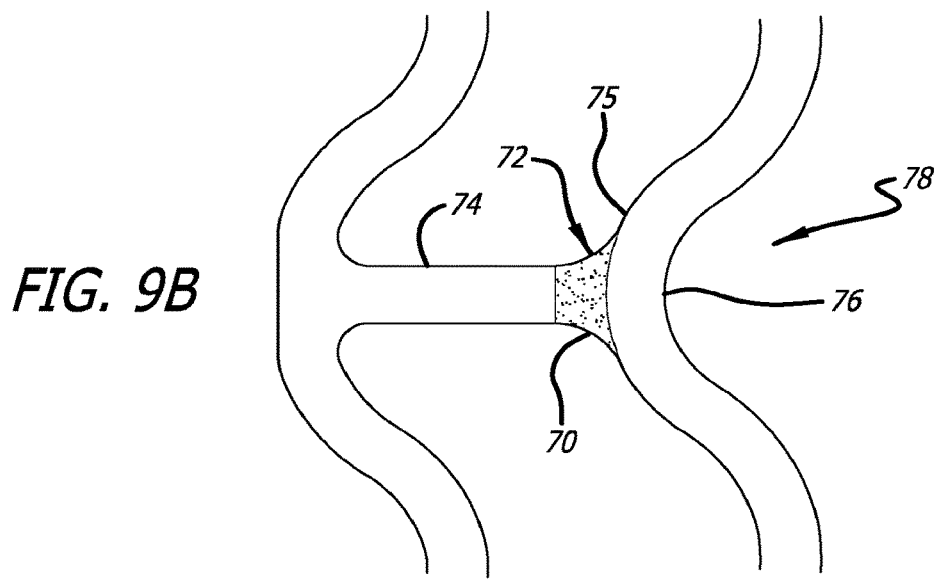
Figure 9C:
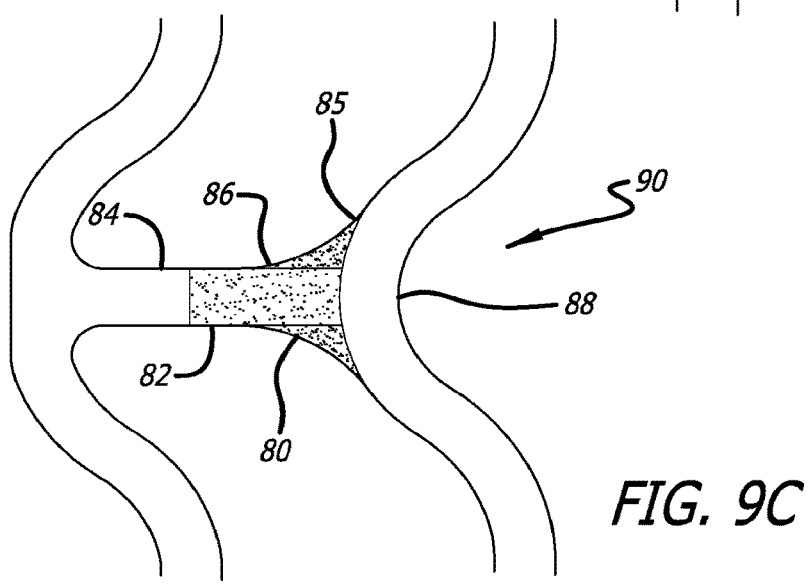

In FIG. 9B, a first shaded area 70 represents the curved portion 72 of the link 74 as it transitions into the curved portion 75 of the valley 76 of the Y-shaped member 78. In one embodiment, the first shaded area 70 is 0.00003 inch$^2$ (0.02 mm$^2$). In FIG. 9C, a second shaded area 80 represents a straight portion 82 of the link 84 plus the curved portion 86 of the link as it transitions into the curved portion 85 of the valley 88 of the Y-shaped member 90. In one embodiment, the second shaded area 80 is 0.00012 inch$^2$ (0.08 mm$^2$). Both the first shaded area 70 and the second shaded area 80 represent structural features that provide less stress in the shaded areas during fatigue loading, resulting in improved Y-shaped member 78, 88 structural fatigue performance.

Figure 10:
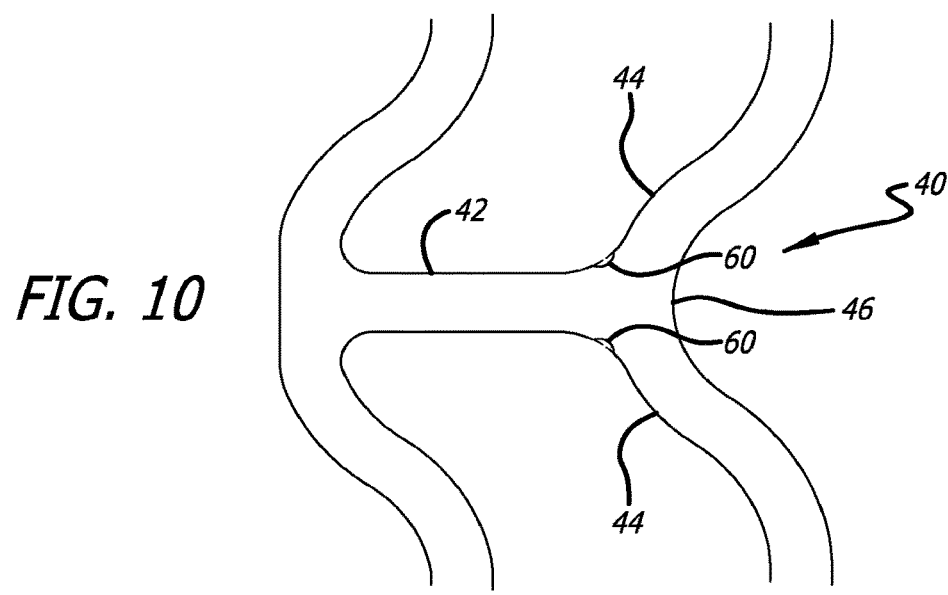
FIG. 10 is an enlarged partial view depicting a Y-shaped member having relief dimples in the curved portions of the Y-shaped member.
Figure 11:
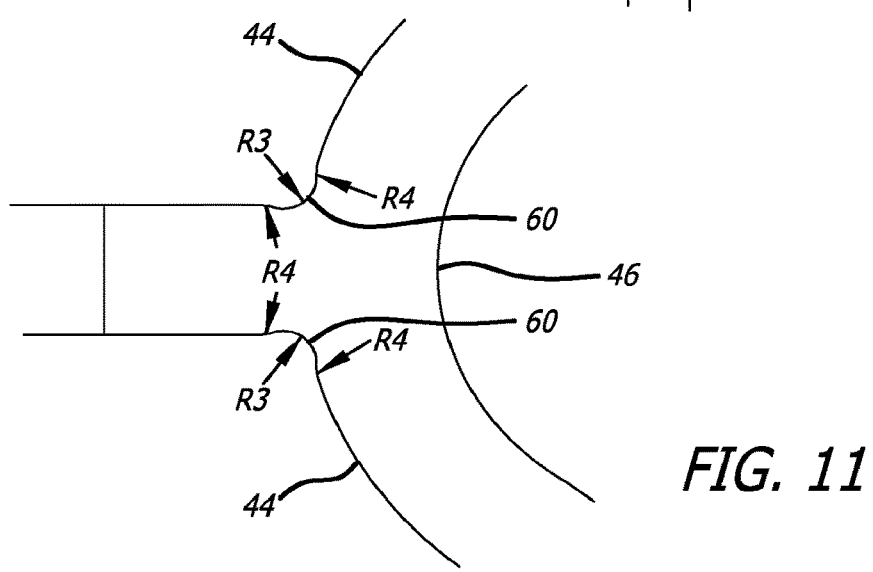
FIG. 11 is an enlarged partial view depicting a Y-shaped member having relief dimples and reversed radii associated with the dimples.

In another embodiment as shown in FIG. 10, the Y-shaped members 40 are formed by the link 42 attaching to a curved portion 44 of a valley 46, which then resembles the Y-shaped member 40. In this embodiment, relief dimples 60 are formed at the curved portion 44 of the valley 46 where the link 42 attaches to the curved portion. Link fatigue factures can occur at the end of a straight section near the link and valley junction where the axially orientated material is weaker and is highly stressed during fatigue loading. The purpose of introducing relief dimples 60 on the curved portion 44 of the valley 46 is to shift the location of this highly stressed area more into the curved portion of the valley where the circumferentially oriented material is stronger and can withstand more stress, thereby improving structural fatigue performance. In the embodiment shown in FIG. 11, the relief dimples 60 have a radius R3 in range of 0.00197 inch (0.05 mm) to 0.00276 inch (0.07 mm). In one embodiment, the relief dimples have a radius R3 of 0.00236 inch (0.06 mm). A reverse radius R4 of 0.000079 inch (0.02 mm) is on either side of the relief dimples in order to have a smooth transition of the relief dimples 60 on the curved portion 44 of valley 46.

While the invention has been illustrated and described herein in terms of its use as an intravascular stent for treating coronary arteries, it will be apparent to those skilled in the art that the stent can be used in other instances such as in treating peripheral vessels. Other modifications and improvements may be made without departing from the scope of the invention.

Other modifications and improvements can be made to the invention without departing from the scope thereof.

We claim:

1. A longitudinally flexible stent for implanting in a body lumen, comprising:
    a first cylindrical ring, a second cylindrical ring, a third cylindrical ring, up to an Nth cylindrical ring, the cylindrical rings being generally independently expandable in the radial direction and generally aligned on a common longitudinal axis;
    each of the cylindrical rings having an undulating pattern of peaks and valleys, the undulating pattern of each of the cylindrical rings being in phase with the undulating pattern of each of the adjacent cylindrical rings;
    each of the cylindrical rings being interconnected by links to one of the adjacent cylindrical rings so that the cylindrical rings form a longitudinally flexible stent;
    a Y-shaped member is formed by one of the links connecting to a first curved portion of a valley, the first curved portion of the valley having a width that is less than a width of a second curved portion of the peaks; and
    wherein a first shaded area is formed where the first curved portion transitions from a straight segment of a link to an arc of the curve of the third curved portion of the valley of the Y-shaped member and wherein the first shaded area is 0.00003 square inch.

2. The stent of claim 1, wherein the width of the first curved portion of the valley is in the range from 0.0073 to 0.0066 inch.

3. The stent of claim 1, wherein each of the cylindrical rings includes at least three peaks and three valleys.

4. The stent of claim 1, wherein the peaks and valleys have a U-shaped configuration.

5. The stent of claim 1, wherein the stent is formed from a polymer material.

6. The stent of claim 1, wherein the stent is formed from a biodegradable material.

* * * * *